United States Patent [19]
Archer et al.

[11] Patent Number: 4,975,245
[45] Date of Patent: Dec. 4, 1990

[54] RECIRCULATING HIGH VELOCITY HOT AIR STERILIZATION PROCESS

[75] Inventors: Virgil L. Archer; M. Keith Cox, both of Dallas, Tex.

[73] Assignee: Archer Aire Industries, Inc., Dallas, Tex.

[21] Appl. No.: 406,964

[22] Filed: Sep. 12, 1989

Related U.S. Application Data

[60] Division of Ser. No. 310,031, Feb. 10, 1989, Pat. No. 4,894,207, which is a continuation-in-part of Ser. No. 915,116, Oct. 3, 1986, abandoned.

[51] Int. Cl.$^5$ .......................... A61L 2/00; A61L 2/04; A61L 2/06
[52] U.S. Cl. ...................................... 422/31; 219/369; 219/374; 422/1; 422/7; 422/28; 422/292
[58] Field of Search ................. 422/1, 7, 28, 292, 295, 422/297, 300; 219/369, 359, 371, 374

[56] References Cited

U.S. PATENT DOCUMENTS

| | | | |
|---|---|---|---|
| 2,480,227 | 8/1949 | Derr | 34/45 |
| 3,839,622 | 10/1974 | Mastin | 219/400 |
| 4,039,776 | 8/1977 | Roderick | 219/401 |
| 4,078,943 | 3/1978 | Saurenman | 422/28 X |
| 4,337,109 | 6/1982 | Brown et al. | 99/401 |
| 4,395,233 | 7/1983 | Smith et al. | 432/176 |
| 4,430,989 | 2/1984 | Narang et al. | 126/273 |
| 4,455,478 | 6/1984 | Guibert | 219/400 |
| 4,581,989 | 4/1986 | Swartley | 99/346 |
| 4,643,303 | 2/1987 | Arp et al. | 422/300 X |

Primary Examiner—Robert J. Hill, Jr.
Assistant Examiner—Amalia L. Santiago
Attorney, Agent, or Firm—Hubbard, Thurman, Turner, Tucker & Harris

[57] ABSTRACT

A recirculating high velocity hot air sterilization device includes a housing having a chamber therein. A corrugated, perforated jet curtain plate is disposed within the chamber and partially defines an air supply plenum positioned outwardly of the chamber, the plenum having an electric heating element operatively positioned therein. Spaced apart from the jet curtain plate within the chamber is a nonperforated deflector plate which extends parallel to the jet curtain plate and may be of a flat or corrugated configuration. A blower is connected to the housing and creates therein a recirculating flow of heated air which sequentially flows into the air supply plenum across the heating element, outwardly in a forward direction through the perforations in the jet curtain plate and into the housing chamber, back into the blower, and then into the air supply plenum. Metal surgical or dental instruments to be sterilized are positioned in one or more wire mesh trays which are removably supported within the housing chamber between the spaced apart from the deflector plate and the jet curtain plate. The flow of heated air through the perforations in the jet curtain plate creates within the chamber a spaced apart series of forwardly travelling, high velocity, heated air impingement jets which operates to rapidly and thoroughly sterilize the instruments.

6 Claims, 4 Drawing Sheets

RECIRCULATING HIGH VELOCITY HOT AIR STERILIZATION PROCESS

CROSS-REFERENCE TO RELATED APPLICATION

This application is a division of application Ser. No. 07/310.031 filed Feb. 10, 1984 now U.S. Pat. No. 4,894,267, which is a continuation-in-part of pending U.S. application Ser. No. 915,116 filed on Oct. 3, 1986, entitled: "Recirculating High Velocity Hot Air Sterilization Device", now abandoned.

BACKGROUND OF THE INVENTION

1. Field of the Invention

The present invention relates to a device and process for the sterilization and depyrogenation of dental and surgical metal instruments. The invention relates, more particularly, to a device and process for the rapid, inexpensive and non-corrosive sterilization and depyrogenation of dental and surgical metal instruments.

2. Description of the Prior Art

In every health profession, the guiding principle "...do good, but do no harm" is as valid today as in the ancient Greece of its author, Hippocrates. Over the years, the second part of this motto was directed at the patient while treatment-related hazards to the practitioner's health were either discounted or accepted stoically. In dentistry, the simplistic attitude that patients — not professionals — acquire treatment-related diseases is giving way to the more realistic concept that operatory personnel are the main targets of viral and bacterial agents of infections.

To demonstrate the central position of dentists in the acquisition and broadcast of nosocomial infectious disease, their rate of hepatitis B infection is four-fold higher than that of the general public. If the dentist is male, he can pass the disease by sexual activity to his wife. If she, or female operatory personnel, incubate the virus during pregnancy, their newborn children have a 90% chance of becoming lifelong carriers of the virus and a 53% chance of dying from liver cancer. Whether male or female, dental personnel harboring hepatitis B virus can pass the disease to patients, especially via blood exiting the finger through cuts.

The recent dramatic rise in the spread of infectious diseases in the United States has resulted in an acute awareness of the potentially grave danger of transmission to health care professionals in general. As noted above, dentists and dental auxiliaries occupy a central position in the acquisition and broadcast of nosocomial infectious disease. The risk, however, extends beyond dentists and dental auxiliaries to the crossover contamination from patient to patient.

For example, it is estimated that there are 200,000 new cases of hepatitis B in the U.S. each year with nearly 1 million chronic carriers. Since 1974, there has been a 234% increase in reported cases of Herpes Simplex II and a 40,350% increase in AIDS cases. Add to these the diseases that can frequently be transmitted, such as gonorrhea, infectious mononucleosis, measles, pneumonia, tetanus, amoebic dysentery and the highly resistant organisms that are reaching the United States from foreign countries, and a frightening scenario emerges.

Recent legal decisions have placed the burden of proof of proper sterilization procedures on the dental office where the possibility of suspected transmission of infection exists. It follows that malpractice insurance carriers may soon require strict adherence to effective and accepted sterilization procedures.

The solution to the problem of contamination with infectious disease in the dental office from patient to dental personnel and from patient to patient is to ensure the complete sterilization and depyrogenation (killing all forms of microbial life: viral and bacterial pathogens including spores) of all instruments.

In the dental office environment, there are several currently accepted means of sterilization. All of the systems currently employed, as discussed below, lack the capability of rapid sterilization of instruments between patients to allow the immediate reuse of the instruments.

The first method of sterilization is known as cold solution sterilization. Cold solution sterilization requires 20 to 30 minutes to disinfect and 10 hours to sterilize (if the solution is fresh and mixed to proper strength). Procedural problems involved with cold solution sterilization are as follows: many currently available solutions will discolor the skin on contact; most available solutions have an offensive odor; dental instruments will rust if they are left in the solutions over an extended period of time; and instruments are often placed in the solution haphazardly with no record of how long they remain. Other limitations concerning the cold solution sterilization system include the fact that the required solutions are expensive and must constantly be replenished.

The second method of sterilization involves the utilization of steam heat. Steam heat sterilization requires 30 to 60 minutes to sterilize. Procedural problems involved with steam heat sterilization are as follows: a central sterilization area is required and a large piece of expensive equipment which can be hazardous to operating personnel is required. Other limitations concerning steam heat sterilization include the fact that the method corrodes, rusts and dulls instruments - particularly where such instruments are of a carbon steel construction.

The third method of sterilization involves the use of alcohol steam. Alcohol steam requires a minimum of 30 minutes to achieve sterilization. Procedural problems involved with alcohol steam sterilization are as follows: a central sterilization area is required; sterilization usually requires the use of "wrapped packs" which necessitate an increase in the number of instruments needed by an office; and the use of "wrapped packs" also lends itself to careless techniques in that packs are often broken into to retrieve one needed instrument if complete packs of all instruments are not available. Other limitations concerning alcohol steam sterilization include the fact that alcohol steam also corrodes instruments, but not to the same degree as steam heat. Additionally, alcohol steam contains formaldehyde - the presence of which constitutes a potential health hazard. Accordingly, purging systems are typically required to exhaust the alcohol steam from the sterilizer cabinet each time its access door is opened.

The fourth method of sterilization involves the use of dry heat. Dry heat sterilization conventionally requires a minimum of 60 minutes to achieve sterilization. With the exception of the purging requirements associated with the presence of formaldehyde, the problems involved with dry heat sterilization are essentially the same as discussed with regard to alcohol steam sterilization since wrapped packs are used. Addtionally, however, the lack of uniform sterilizing heat distribution, and a corresponding non-uniform temperature pattern within the sterilizing cabinetry, render the validation of the sterilization process somewhat difficult.

The fifth method of sterilization involves the use of ethylene oxide gas. The size, expense and sophistication of this process and the necessary equipment, however, limit its use to commercial large volume sterilization.

The sixth method of sterilization involves the use of heat transfer with glass beads, sand, glass, ball bearings and other similar items being used as a heat-transfer medium. Heat transfer sterilization requires 10 seconds at 450° to achieve sterilization. This method has no known procedural problems. A major limitation concerning heat transfer sterilization, however, is the fact that a small unit is used which is suitable only for small endodontic files, broaches and other similar items.

Among the currently employed sterilization systems, the heat transfer system is the only one with the capability of rapid sterilization of instruments between patients and its small capacity limits its use in the dental office.

Thus, a need exists in the art for a rapid, safe, inexpensive and non-corrosive sterilization method and device that provides for the sterilization and depyrogenation of procedural instruments in health care facilities and especially the dental office.

SUMMARY OF THE INVENTION

The device for the sterilization and depyrogenation of dental and surgical metal instruments of the present invention avoids the above-mentioned disadvantages which are characteristic of the prior art. More specifically, the device of the present invention provides a means for the sterilization of dental and surgical metal instruments that is rapid, non-corrosive, clean, inexpensive and efficient. The device of the present invention is a dry-heat sterilizer that utilizes the speed of heat transfer principles in a unit large enough to accommodate dental instruments and other small surgical instruments. The device is also useful for the sterilization and depyrogenation of dental and surgical implants.

The sterilization device of the present invention has high heat transfer efficiency and reduces the time required to sterilize dental and surgical metal instruments over that required by conventional sterilization devices. The sterilization device of the present invention provides complete sterilization and depyrogenation, preferably, in less than 3 minutes utilizing a process in which deturbulized air, moving at, preferably, 1500 to 3000 feet per minute, is heated to a sterilizing temperature of, preferably, 350° to 400° F.

The sterilization device of the present invention provides for instrument sterilization between treatment of each patient thereby eliminating the greatest source of contamination from patient to personnel as well as cross contamination from patient to patient.

The sterilization device of the present invention and its variations may be used in dental offices, medical offices and clinics particularly where minor surgical procedures are performed; in oral surgery offices; in hospitals and other health care facilities; in emergency rooms; in Dental, Medical and Veterinary Medical Schools; in schools of Dental Hygiene; in schools of Medical Technology; in schools of Physical Therapy; in Military Health Care Facilities; and, in other environments where individuals could be subjected to contamination or cross infection including, but not limited to, ear piercing, electrolysis and skin care.

It is an object of the present invention to provide a device for the sterilization and depyrogenation of metal dental instruments that is 10 to 20 times faster than any other currently employed system of sterilization in the dental office; completely safe to operating personnel; durable and lasts the lifetime of a dental office with only the simple replacement of a fan motor or heating element; simple in operation; more inexpensive than other types of sterilization devices; less harmful to instruments than any other types of sterilization; small enough for use in the operatory and does not require a central sterilization area; inexpensive enough to allow for use of multiple units placed at convenient locations where instruments are used; maintenance free; preferably insulated to protect the outside of the unit from becoming hot; and preferably constructed with external stainless steel to provide a lifetime non-corrosive surface that can be disinfected with a wipe solution.

It is another object of the present invention to provide a device that reliably provides total sterilization and depyrogenation of dental and surgical metal instruments.

It is an additional object of the present invention to provide a device for the sterilization and depyrogenation of dental and surgical metal instruments that releases no heat or odor and does not require the use or addition of chemicals.

These and other objects are achieved by the recirculating high velocity hot air sterilization device of the present invention.

The device of the present invention includes an enclosure or housing which defines a sterilization chamber and a plenum chamber with a blower disposed in the plenum chamber. A perforated jet curtain plate is disposed within the sterilization chamber and partially defines an air supply plenum. A heating element is disposed within the air supply plenum. Means are provided for fluid communication between the outlet port of the blower, the air supply plenum, the sterilization chamber, and the intake port of the blower. The blower recirculates air throughout the device at a high temperature and a high velocity and sterilizes dental and surgical metal instruments that may be placed within the device.

The blower forces heated air upwardly through the perforations in the jet curtain plate to form within the sterilization chamber a mutually spaced series of upwardly directed high velocity heated air impingement jets. Positioned within the sterilization chamber in an upwardly spaced relationship with the jet curtain plate is a corrugated, nonperforated air deflector plate which extends generally parallel to the jet curtain plate. The corrugated deflector plate is positioned in the path of the upwardly directed impingement jets and serves to intercept, laterally offset and rearwardly deflect such jets toward the jet curtain plate. The instruments to be sterilized are supported within a wire mesh tray which is removably positioned within the sterilization chamber between and spaced apart from the corrugated deflector plate and jet curtain plate.

Some of the upwardly directed impingement jets strike lower surface portions of the supported instruments, while other impingement jets bypass the supported instruments and impinge upon the upper deflector plate. These jets which bypass the supported instruments impinge upon the deflector plate, are laterally offset, and then are rearwardly deflected toward the supported instruments. The deflected jets impinge upon upper surface portions of the supported instruments and create a high degree of heated air turbulence adjacent thereto. The combination of high velocity heated air impingement air on both sides of the instruments, and the resulting high degree of heated air turbulence, sterilizes and depyrogenates the instruments in a small fraction of the time normally required in conventional sterilizing apparatus. In addition to their jet-forming and deflecting functions, the corrugated jet curtain plate and air deflector plate additionally function in a unique manner to facilitate an extremely uniform air distribution flow within the sterilizing chamber of both the originally formed impingements jets and the rearwardly deflected impingement jets.

In an alternate embodiment of the present invention, the corrugated upper deflector plate is replaced with a flat deflector plate. In developing the present invention, it has been found that the previously described impingement air sterilization technique may also be performed using this alternate flat deflector plate in conjunction with the corrugated jet curtain plate disposed beneath it. The heated air impingement jets discharge from the jet curtain plate and bypassing the instruments supported within the sterilization chamber are rearwardly deflected, and somewhat laterally diffused, by the flat deflector plate so that the deflected jets impinge upon upper surfaces of the supported instruments being sterilized. Although the flat deflector plate is somewhat less efficient than its corrugated counterpart with regard to the reverse flow of heated impingement air, this slight decrease in efficiency may be easily offset by providing the blower with a somewhat larger motor. With such increase in blower motor size, the same complete and very rapid impingement sterilizing is still performed, and there are no appreciable "cold" or "dead" spots within the sterilization chamber.

In a further alternate embodiment of the present invention the corrugated jet and deflector plates (or the corrugated jet plate and the flat deflector plate, as the case may be) are vertically disposed, and are positioned in a facing relationship on opposite sides of the sterilization chamber so that the initial and deflected flows of the high velocity heated air jets are generally horizontal. The sterilization chamber has disposed therein multiple wire mesh trays adapted to support metal surgical or dental instruments which may be directly exposed to the sterilizing air flow or wrapped in a suitable covering material such as paper or muslin.

BRIEF DESCRIPTION OF THE DRAWINGS

In describing the invention, reference will be made to the accompanying drawings in which.

DETAILED DESCRIPTION OF THE PREFERRED EMBODIMENTS

Figure 1:
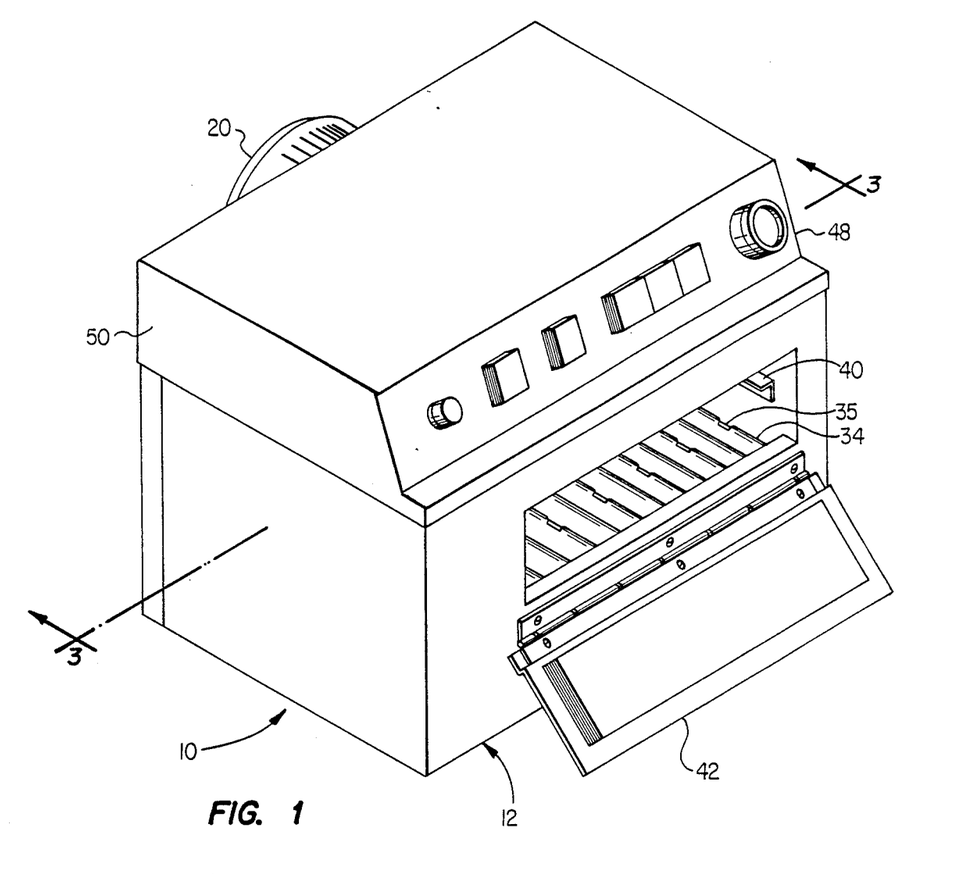
FIG. 1 is a perspective view of a preferred embodiment of the recirculating high velocity hot air sterilization device of the present invention.

Referring now to the drawings and, in particular, FIG. 1, a preferred recirculating high velocity hot air sterilization device generally indicated at 10 is defined by an enclosure or housing 12. As shown more clearly in FIGS. 3 and 4, the enclosure 12 includes a plurality of walls 14. Walls 14 are preferably insulated. A partition 16 divides the enclosure 12 into a sterilization chamber 18 and a plenum chamber 25. A blower 20 is disposed within the plenum chamber 25 of enclosure 12. The intake port 22 of blower 20 is in fluid communication with sterilization chamber 18. The outlet port 24 of blower 20 is in fluid communication with duct chamber 26. A wall 27 separates the duct chamber 26 from the sterilization chamber 18. An airflow opening 28 is provided within wall 27 to allow for fluid communication between duct chamber 26 and sterilization chamber 18.

Figure 3:
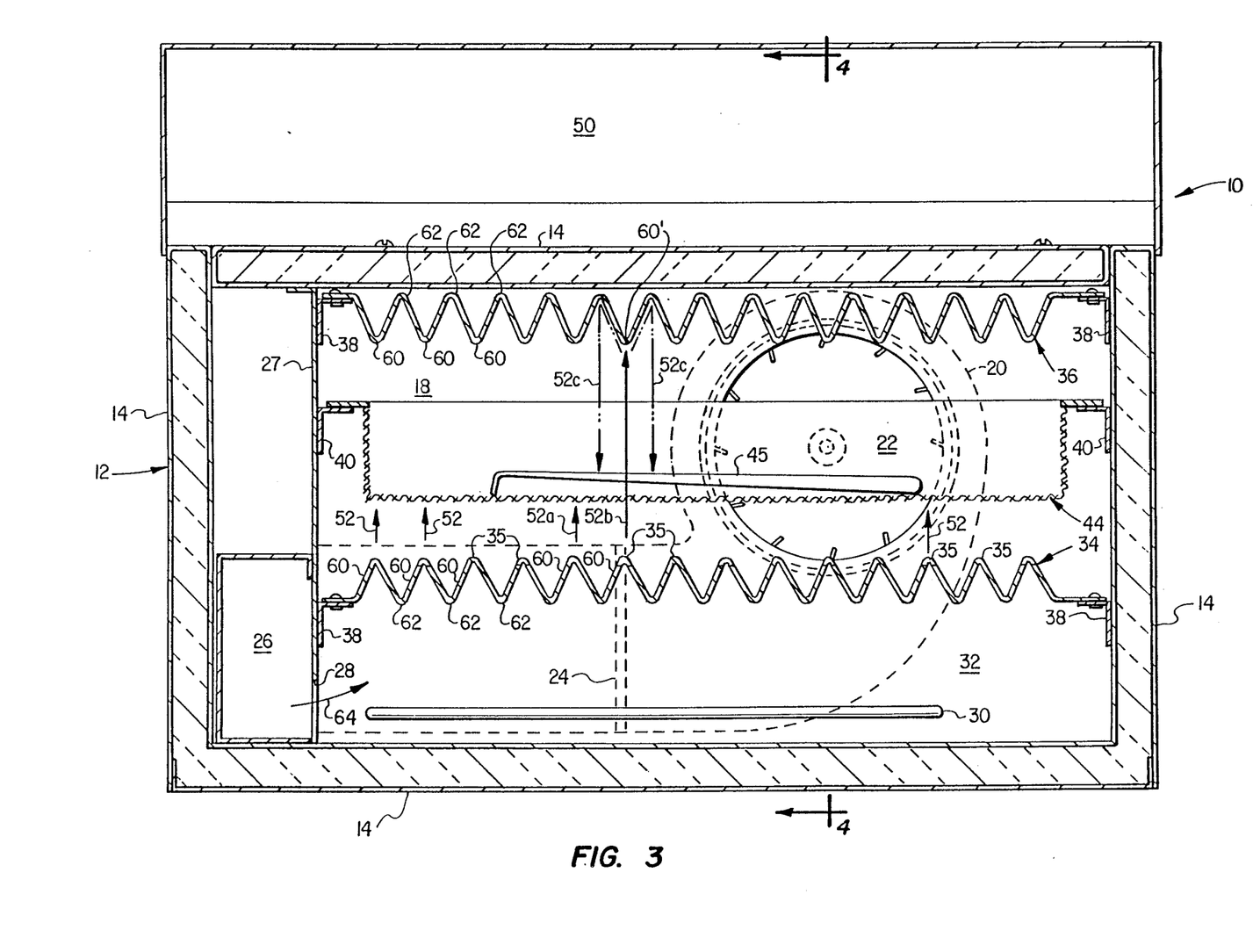
FIG. 3 is a section taken along line 3—3 of FIG. 1.

As shown most clearly in FIG. 3, a perforated jet curtain plate 34 is provided within enclosure 12. The perforated jet curtain plate 34 partially defines an air supply plenum 32 within sterilization chamber 18. A heating element 30 is provided within plenum 32 to heat the air entering the plenum through air flow opening 28. An upper non-perforated jet curtain or air deflector plate 36 may preferably be disposed within sterilization chamber 18. Each of perforated jet curtain plate 34 and non-perforated jet curtain plate 36 are rigidly supported within enclosure 12 by a plurality of support flanges 38. A plurality of support flanges 40 are provided between perforated jet curtain plate 34 and nonperforated jet curtain plate 36 to removably support an open wire mesh tray 44 containing metal dental or surgical metal instruments 45. A door 42 is provided within enclosure 12. Door 42 is openable to provide access to sterilization chamber 18. Door 42 provides an air-tight seal and serves to seal the sterilization chamber 18 from the outside environment.

The perforated jet curtain plate 34 is mounted within housing 10 and is spaced apart from and above the heating element 30, and downwardly from the upper plate 36. As shown most clearly in FIGS. 1 and 4, the perforated jet curtain plate 34 contains an array of elongated, generally rectangular slots 35 through which turbulized air from the air supply plenum 32 is unturbulized and directed in a series of heated air impingement jets 52 (FIG. 3) toward the dental or surgical metal instruments 45 supported in tray 44. The rectangular slots 35 of the perforated jet curtain plate 34 vary in width, length and number in relation to the horsepower of the blower to yield jets of air emanating from the slots 35 at a velocity of from 1500 to 3000 feet/minute. The velocity of air emanating from the slots 35 may be measured by a Dwyer Air Velocity Calculator: #460 Air Meter made by Dwyer Instruments, Inc., Michigan City, Ind. under U.S. Pat. No. 2,993,374. The velocity of the air emanating from the slots 35 depends upon the ratio of the area of the output port 24 of the blower 20 to the area of the slots 35. The velocity of the air emanating from the slots 35 also depends upon the horsepower and speed of the blower 20. Those skilled in the art will recognize that these variables may be adjusted through routine experimentation to achieve a desired velocity of air emanating from the slots 35.

The perforated jet curtain plate 34 distributes heat uniformly and efficiently to the instruments 45 being supported and sterilized in the tray 44. The unturbulized air emanating from the slots 35 of the perforated jet curtain plate 34 travels through the sterilization chamber and is reflected rearwardly from the corrugated, non-perforated jet curtain plate 36. The air is then circulated back through the blower 20 to again enter the duct chamber 26, the air supply plenum 32 and the sterilization chamber 18, in sequence. When the blower 20 is operating, a continuous stream of air flows through the entire system. Turbulized air from the blower 20 scrubs the heating element 30 and picks up heat which is then delivered to the instruments by the high velocity jets of air emanating from the slots 35 of the perforated jet curtain plate 34.

Figure 4:
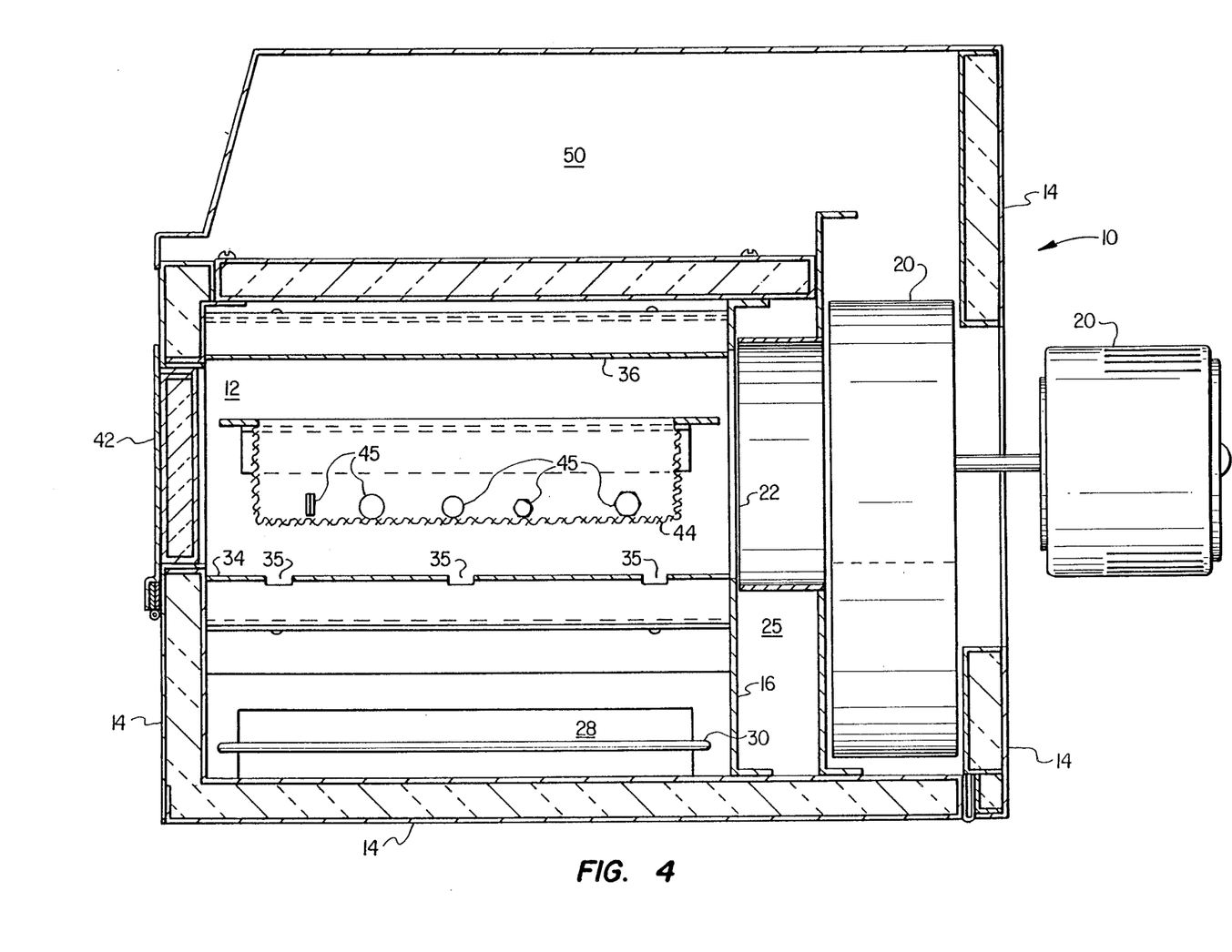
FIG. 4 is a section taken along line 4—4 of FIG. 3.

The perforated jet curtain plate 34 is uniquely corrugated in a pattern of rounded v-shaped corrugations alternately v-shaped and inverted v-shaped. As shown in FIGS. 1 and 4, the slots 35 of the perforated jet curtain plate 34 are disposed in the crests rather than the troughs of the v-shaped corrugations.

The extreme efficiency of jets of high velocity heated air emanating from the slots 35 of the perforated jet curtain plate 34 speeds the sterilization and depyrogenation of the dental or surgical metal instruments supported in the tray 44 without requiring an extreme differential between the temperature of the heating element 30 and the temperature of the air. Unused heat contained in the recirculating air is conserved by the device of the present invention which, as noted previously, may be insulated to reduce heat loss. It is therefore possible to provide quick efficient sterilization and depyrogenation of dental or surgical metal instruments with air heated to about 350° to 400° F., and preferably 350° to 375° F., without requiring the heating element 30 to run at full capacity, which conserves energy and increases the life of the instruments. It is well known by those skilled in the art that the alloy arrangements in dental and surgical metal instruments are disrupted when exposed to temperatures in excess of 400° F.

As shown in FIG. 1, a control panel 48 is disposed on the external portion of the control zone 50. As shown in FIGS. 1, 3 and 4, control zone 50 is located above sterilization chamber 18. Control zone 50, preferably, contains circuitry for controlling blower 20 and heating element 30. Control zone 50 also preferably includes conventional timing circuitry to provide for various timing cycles. It has been found that sterilization is a function of time, temperature and velocity of air. The longer the time, the higher the temperature and the higher the velocity of air, the more likely complete sterilization has been achieved It has been discovered through testing that at a temperature of from 350° F. to 400° F. and a velocity of 1500 feet/minute to 3000 feet/minute, unwrapped instruments are completely sterilized in approximately 3 minutes, paper wrapped instruments are sterilized in approximately 8 minutes and towel wrapped surgical instruments are sterilized in approximately 12 minutes.

The present invention will be described in more detail with reference to the following example. This example is merely illustrative of the present invention and is not intended to be limiting.

Example 1

Tests were conducted using 12 typical dental instruments through controlled heat, time and velocity sequences. The results were recorded utilizing biological validation of sterilization. Two spore strips containing Bacillus stearothermophilus and Bacillus subtilis, var. niger, were placed with the instruments to be sterilized and subjected to each time and heat cycle. Velocity was maintained constant at the maximum practically obtainable.

The spore strips, along with a control strip for each two tested strips, were cultured and incubated for 48 hours in trypticase soy broth at temperatures of 37° C. and 57° C. Observed growth was checked microscopically and gram stained. The tests were blinded.

After establishing a time, temperature and air velocity combination which was subjectively viewed to be optimal for the purposes of practical dental usage, spore strip and spore suspension tests were repeatedly performed as verification.

A combination of temperature and air velocity was sought that would, as a goal, allow sterilization in three minutes or less.

The American Dental Association's "Proposed American National Standard/American Dental Association Specification No. 64 for Dental Explorers" states in Par. 5.3 "The instrument when tested in accordance with Par. 6.2 shall show no alteration to its physical appearance. The dry heat test should be carried out on the instrument prior to the tests for the union between working end and handle." Par. 6.2 states that "Subject this instrument to dry heat at a temperature of 180° C. (356° F.) for 60 minutes."

If heat of 356° F. for one hour, which will core heat the metal, will not damage the instrument, it was theorized that a higher temperature and a drastically reduced time would not core heat the instrument and would therefore not harm the metal.

New Hu-Friedy™ and American Dental Instruments™ instruments were placed in the device of the present invention and subjected to recirculating air heated to 375° F. at a velocity of 1500 to 3000 feet/minute for a three minute cycle. This test was repeated 100 times. The following observations were made:
1. Complete and total sterilization was achieved.
2. There was no undesirable alteration to the appearance of the instruments.
3. There was no decrease in the tactile sense of the instruments.
4. There was no apparent loss of temper of the instruments.

Thus, the metal of the instruments was not harmed while, at the same time, complete sterilization was achieved.

As can be seen from the foregoing, the sterilization device 10 of the present invention provides for the complete and extremely rapid sterilization of the instruments 45 in a simple, reliable, and relatively inexpensive manner utilizing only recirculating heated air within the housing 12. Such rapid sterilization is achieved by a unique combination of structural and operational features of the device 10 which will now be described in greater detail with particular reference to FIG. 3.

It should first be noted that, with the exception of the rectangular air supply slots 35 formed in the lower jet curtain plate 34, the cross-sectional configurations of the corrugated plates 34 and 36 are substantially identical. Each of the corrugated cross-sections of the plates 34 and 36 is defined by alternating series of parallel ridges 60 and 62 which respectively project in laterally opposite directions on the plate upon which such ridges are formed. The ridges ("crests") on the lower plate 34 project upwardly, while the ridges 60 on the upper plate 36 project downwardly. The identically configured plates 34 and 36 are aligned within the housing 12 so that they are essentially mirror images of one another. More specifically, as can be seen in FIG. 3, each of the ridges 60 of the lower plate 34 is horizontally aligned with a corresponding downwardly projecting ridge 60 on the upper deflector plate 36.

During operation of the sterilizing device 10, air 64 is forced by the blower 20 through the opening 28 into the air supply plenum 32, the entering air being heated by the heating element 30. As previously described, the air heated within the plenum 32 by the heating element 30 is forced upwardly through the rectangular air supply slots 35 formed in the upwardly projecting ridges or crests 60 in the jet curtain plate 34, the rectangular slots 35 being elongated in a direction parallel to the ridges 60. The heated air 64 is discharged upwardly through the slots 35 in the form of the high velocity, heated air impingement jets 52. By a unique cooperation between the aligned plate members 34 and 36, these high velocity impingement air jets 52 are caused to simultaneously impinge upon upper and lower surfaces of the instruments 45 supported in the wire mesh tray 44.

To illustrate this unique dual impingement air flow pattern, reference is made to the two representative impingement air jets $52_a$ and $52_b$ depicted in FIG. 3. Depending upon the relative orientation of the instruments 45 in the mesh tray 44, various of the upwardly directed jets 52 will impinge upon lower surface portions of the instruments, while others of the jets 52 will bypass the instruments and continue their high velocity travel toward the upper deflector plate 36.

For purposes of illustration, let it be assumed that the representative jet $52_a$ impinges upon a lower surface portion of one of the instruments 45, and that the other representative jet $52_b$ bypasses such instrument and impinges upon the downwardly projecting ridge 60' (of plate 36) which is aligned with and spaced upwardly from the ridge 60 (of plate 34) from which the jet $52_b$ is upwardly discharged. When the jet $52_b$ impinges upon the downwardly projecting ridge 60' it is divided by the ridge 60' into two jet portions $52_c$ which are laterally shifted relative to the original jet path. The jet portions $52_c$ are then downwardly or rearwardly deflected by the upper plate 36 at a high velocity toward the instruments 45 in tray 44.

The laterally offset and rearwardly deflected jet portions $52_c$ then impinge upon upper surface portions of the instruments 45. This dual impingement process is, of course, continuously repeated at other locations within the housing by other sets of upwardly flowing and rearwardly deflected impingement jets.

The cooperation between the upwardly directed and rearwardly deflected impingement jets not only creates a continuous high velocity heated air impingement on both sides of the supported instruments, but also creates a high degree of heated air turbulence in their immediate vicinity. Such enveloping impingement and concomitant turbulence serve to very rapidly "drive" heat from the jets 52 into the instruments 45 to quickly and completely sterilize and depyrogenate them. After the jets 52 have impinged upon and created a highly turbulent sterilizing air pattern around the instruments 45, the heated air around the instruments is drawn rearwardly into the inlet 22 of blower 20 (i.e., across the instruments in a direction transverse to the jets 52 as illustrated in FIG. 3) and returned to the air supply plenum 32 via the wall opening 28 as previously described.

The corrugations in the plate members 34 and 36 perform a variety of unique and advantageous functions in the sterilizing device 10. For example, the corrugations in the lower jet curtain plate 34 not only cooperate with the air slots 35 to define jet-forming means, but they also serve as balancing means to facilitate the very even distribution of turbulized, heated supply air to the lower surface of the jet curtain plate 34. More specifically, as compared to a variety of conventional planar air supply plates with circular jet columnating openings formed therein, the corrugations in the nonplanar plate 34 serve to uniformly "capture" supply air within the air supply plenum 32 and evenly distribute the captured air to the slots 35. The result of the balancing role played by the corrugations in plate 34 is that, across the length and width of the plate 34, the jets 52 have substantially identical velocities and steady state flow volumes. This balancing effect of the corrugations in the jet curtain plate 34 is further enhanced by the elongated rectangular configurations of the air slots 35 which, to a marked degree, further enhance the velocity and flow volume uniformity of the upwardly directed impingement jets 52.

A similar flow balancing function is also performed by the corrugations in the upper deflector plate 36 in a manner such that the rearwardly deflected jet portions are substantially uniform in both velocity and steady state flow volume. Additionally, these upper corrugations laterally deflect the upwardly directed jets 52 which impinge thereon in a very even and controlled manner so that the deflected jet portions create a very uniform downwardly directed flow pattern. The combinative result of the balancing functions performed by the upper and lower plate corrugations is that the overall upward and downward air flow pattern is quite uniform across the length and width of the sterilization chamber 18 so that there are no appreciable "dead" or "cold" spots therein Accordingly, regardless of where in the tray 44 a particular instrument 45 is placed, the rapid, uniform and complete sterilization and depyrogenation of such instrument is assured.

Figures 2, 5:
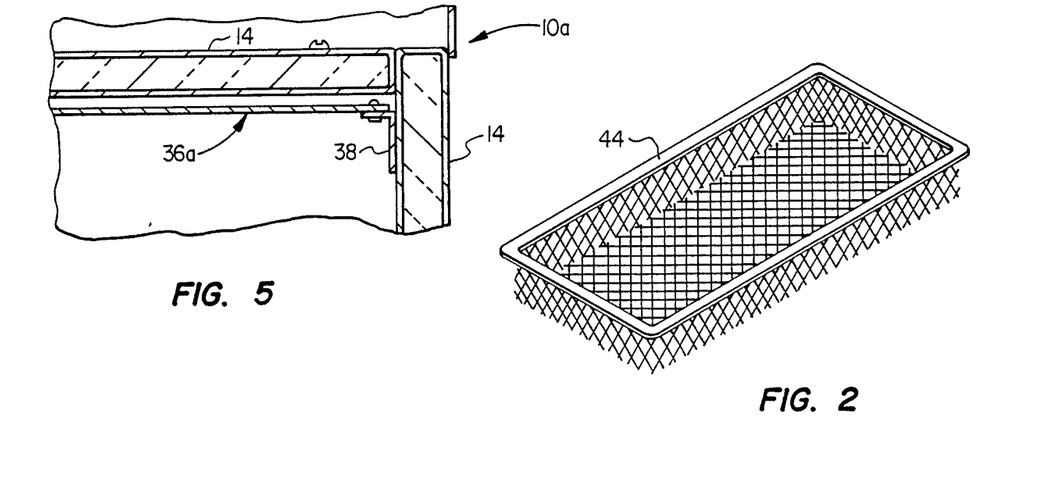
FIG. 2 is a perspective view of a perforated tray for holding items to be sterilized.
FIG. 5 is a partial cross-sectional view taken along line 3—3 of FIG. 1 and illustrates an alternate embodiment of the sterilization device in which the corrugated upper deflector is replaced with a flat deflector plate.

This extremely rapid and uniform sterilization process may also be carried out in the present invention, in an alternate embodiment $10_a$ of the sterilizer (FIG. 5), by utilizing a flat upper deflector plate $36_a$ instead of the previously described corrugated deflector plate 36. While the flat deflector plate $36_a$ is of a simpler construction and somewhat less expensive to manufacture than the corrugated deflector plate 36, it is also somewhat less efficient in producing the rearwardly deflected impingement air flow which is driven against the upper surfaces of the supported instruments. However, it has been found that this decrease in efficiency may be easily overcome by simply increasing the size of the blower motor. With such increase in the blower motor size, the supported instruments are still rapidly sterilized and depyrogenated and subjected to heated air impingement and a high degree of air turbulence on both sides thereof. Moreover, it has been learned that even when the alternate flat deflector plate $36_a$ is utilized, there are no appreciable "cold" or "dead" spaces within the sterilization chamber. Thus, regardless of where in the wire mesh tray 44 a particular instrument 45 is placed, the rapid, uniform and complete sterilization and depyrogenation of such instrument is assured.

Figure 6:
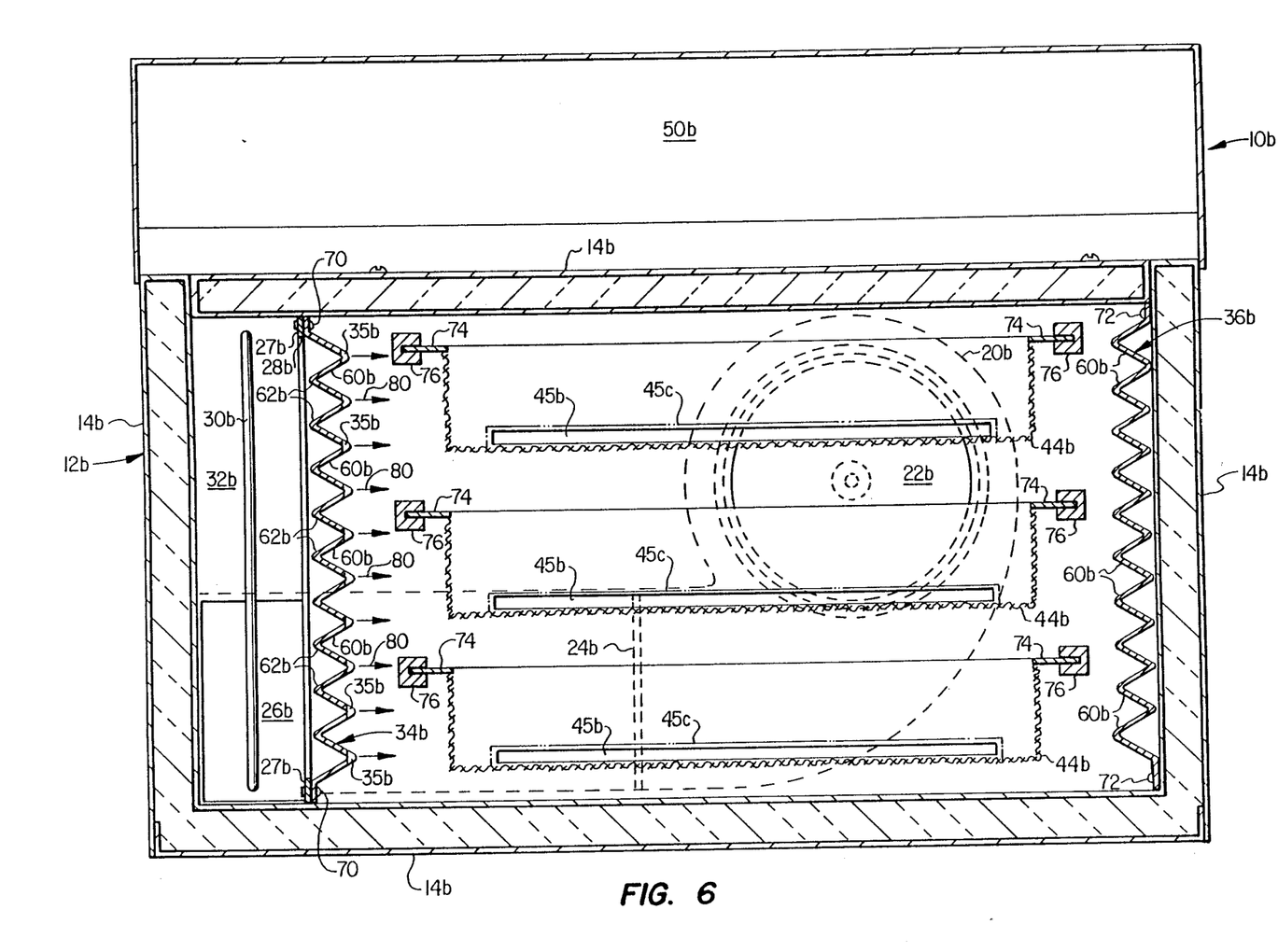
FIG. 6 is a cross-sectional view, similar to that in FIG. 3, taken through an alternate embodiment of the sterilizing device in which the corrugated jet and deflector plates are horizontally disposed within the sterilizer cabinet.

In FIG. 6 there is depicted a further alternate embodiment $10_b$ of the sterilizer 10, the components similar to those of sterilizer 10 being given the same reference numerals with the subscript "b". The basic alteration made to the modified sterilizer $10_b$ is that the corrugated jet curtain and deflector plates $34_b$ and $36_b$ are vertically disposed in a horizontally spaced, parallel relationship within the housing $12_b$, and a vertically spaced series of three wire mesh support trays $44_b$ are positioned within the housing between the plates $34_b$ and $36_b$. The plenum $32_b$ (FIG. 3) is relocated to the space between the vertical interior wall $27_b$ and the left housing wall $14_b$ and the supply opening $28_b$ is formed in the vertical interior wall $27_b$. The heating element $30_b$ is also repositioned to within the relocated plenum $32_b$. Jet curtain plate $34_b$ is vertically secured to the wall $27_b$, over the opening $28_b$ therein, by means of suitable fastening elements 70. Deflector plate $36_b$ is vertically secured to the interior surface of the right housing wall by means of suitable fastening elements 72. The upper peripheral flanges 74 of the trays $44_b$ are removably supported within suitable support channels 76 appropriately mounted within the housing. The trays $44_b$ are adapted to hold dental or surgical instruments $45_b$ which are representatively wrapped in a suitable material $45_c$ such as paper or muslin.

During operation of the modified sterilizer $10_b$, recirculated air is delivered by the fan $20_b$ to the relocated plenum $32_b$, and is forced rightwardly through the wall opening $28_b$ and outwardly through the openings $35_b$ in jet plate $34_b$ to form a series of horizontal, high velocity heated air jets 80. Some of the jets 80 impinge upon the wrapped instruments $45_b$, while the balance of the horizontally directed jets impinge upon the corrugated deflector plate $36_b$, are laterally offset, and rearwardly deflected for impingement upon the instruments as previously described in conjunction with the sterilizer 10. If desired, the corrugated deflector plate $36_b$ may be replaced with a flat deflector plate. Alternatively, the plate $36_b$ could simply be removed, and the interior metal surface of the right housing wall $14_b$ used as a flat deflection surface.

While preferred embodiments of the present invention have been described in detail and with reference to specific examples thereof, it will be apparent to persons skilled in the art that various changes and modifications can be made therein without departing from the spirit and scope thereof as defined by the following claims.

What is claimed is:

1. A method of sterilizing objects, comprising the steps of:
    creating in a sterilizing chamber of a housing a mutually spaced series of high velocity heated air impingement jets flowing generally in a first direction;
    providing a wall member in said sterilizing chamber having a side surface portion in a spaced, opposing relationship with said heated air jets;
    utilizing said side surface portion to intercept and rearwardly deflect at least some of said jets;
    positioning an object to be sterilized by said heated air jets in a manner such that a first surface portion thereof is impinged by a jet flowing in said first direction and a generally opposite surface portion thereof is impinged by a rearwardly deflected jet;
    continuously enveloping said object in a turbulent layer of heated air formed by said jet flowing in said first direction and said rearwardly deflected jet;
    drawing air from the turbulent layer of heater air across said object in a direction generally transverse to said air impingement jets and flowing the air outwardly from said sterilizing chamber;
    heating to a predetermined sterilizing temperature the air outwardly drawn from said sterilizing chamber; and
    recirculating the heated air sequentially through a spaced series of openings to create said air impingement jets.

2. The method of claim 1 wherein:
    said wall member of said providing step has a corrugated side surface portion.

3. The method of claim 2 wherein:
    said providing step includes positioning said wall member within said housing to define a boundary of said sterilizing chamber, and
    said creating step includes the steps of providing a perforated jet curtain plate, positioning said jet curtain plate within said sterilizing chamber so that said jet curtain plate is in a spaced, generally parallel relationship with said wall member and partially defines an air supply plenum, and causing a flow of heated, recirculating air within said housing which sequentially flows into said air supply plenum, through said jet curtain plate toward said wall member, against said wall member, and back into said air supply plenum.

4. The method of claim 3 wherein:
    said step of providing a perforated jet curtain plate is performed by providing a corrugated jet curtain plate having a cross-sectional configuration substantially identical to that of said wall member, and forming air slot openings in ridge portions of said corrugated jet curtain plate said ridge portions projecting in the same direction, and
    said step of positioning said jet curtain plate is performed in a manner such that said ridge portions face said wall member.

5. The method of claim 4 wherein:
    said step of positioning said jet curtain plate includes aligning said jet curtain plate with said wall member so that the facing surfaces of said jet curtain plate and said wall member are essentially mirror images of one another.

6. The method of claim 1 wherein:
    in said creating step, said jets flowing in said first direction have velocities in the range of from approximately 1500 feet per minute to approximately 3000 feet per minute, and temperatures in the range of from approximately 350° F. to approximately 400° F.

* * * * *